United States Patent [19]

Raynor et al.

[11] Patent Number: 5,319,133

[45] Date of Patent: Jun. 7, 1994

[54] ISOCYANATES AND THEIR PREPARATION USING HYPOCHLOROUS ACID

[75] Inventors: Robert J. Raynor, North Branford; Thomas A. Knowles, Cheshire, both of Conn.

[73] Assignee: Olin Corporation, Cheshire, Conn.

[21] Appl. No.: 997,376

[22] Filed: Dec. 28, 1992

[51] Int. Cl.$^5$ ........................................ C07C 263/00
[52] U.S. Cl. .................................. 560/338; 560/330; 560/355; 564/123; 564/152; 564/192; 564/215
[58] Field of Search .................. 560/338, 355, 330; 564/123, 152, 192, 215

[56] References Cited

U.S. PATENT DOCUMENTS

| | | | |
|---|---|---|---|
| 2,640,846 | 6/1953 | Hurwitz et al. | 560/338 |
| 3,483,242 | 12/1969 | Brownstein et al. | 560/338 |
| 4,203,916 | 5/1980 | Zengel et al. | 560/344 |
| 4,238,404 | 12/1980 | Zengel et al. | 560/338 |
| 4,259,258 | 3/1981 | Zengel et al. | 560/800 |
| 4,282,167 | 8/1981 | Sy et al. | 560/338 |
| 4,321,402 | 3/1982 | Ryu et al. | 560/24 |
| 4,418,211 | 11/1983 | Zengel et al. | 564/40 |
| 4,486,603 | 12/1984 | Zengel et al. | 564/461 |
| 5,068,408 | 11/1991 | Raynor et al. | 560/338 X |
| 5,070,200 | 12/1991 | Raynor et al. | 544/242 |

OTHER PUBLICATIONS

Lee et al, *Tetrahedron Letters*, No. 20, pp. 1641–1644, (1976).

Anita O. Sy and Joseph W. Raksis, *Tetrahedron Letters*, vol. 21, pp. 2223–2226, (1980).

*Primary Examiner*—José G. Dees
*Assistant Examiner*—Vera C. Clarke
*Attorney, Agent, or Firm*—Dale L. Carlson

[57] ABSTRACT

The present invention relates to a process for preparation of an isocyanate comprising (a) reacting an amide with an aqueous solution of hypochlorous acid in the presence of an water-immiscible organic solvent to produce an N-chloro amide; and (b) reacting said N-chloro amide with a base in the presence of a phase transfer catalyst and a water immiscible organic solvent to produce an isocyanate.

8 Claims, No Drawings

ISOCYANATES AND THEIR PREPARATION USING HYPOCHLOROUS ACID

BACKGROUND OF THE INVENTION

1. Field of the Invention

The present invention relates generally to the preparation of isocyanates and, more specifically, to a low temperature process for the preparation of an isocyanate from an amide using hypochlorous acid.

2. Background of the Invention

Heretofore, the commercial method of choice for the manufacture of isocyanates has been a gas phase conversion by means of the phosgenation of amines. An example of the use of this methodology for the production of isocyanates is provided in U.S. Pat. No. 4,321,402. Unfortunately, phosgene methodology is expensive in view of the cost of the amine raw materials and the risk associated with the use of highly toxic phosgene gas. Non-phosgene routes to the production of isocyanates are highly sought after by the isocyanates manufacturing community.

One alternative to the use of phosgenation is carbonylation as disclosed in the above-mentioned '402 patent. However, this method utilizes high pressure reaction equipment and expensive carbon monoxide as a reactant, and the method typically uses potentially toxic catalysts such as selenium.

Another alternative is the well-known Hofmann rearrangement reaction entailing the base catalyzed rearrangement of N-halo amides to isocyanates. This reaction is typically conducted in single step without isolating the N-halo amide intermediate before it is reacted and converted into an isocyanate. The isocyanate is not Produced and isolated directly but requires the isocyanate to be trapped as a urea and/or a carbamate, which is then in turn converted to the desired isocyanate by hydrolysis and/or pyrolysis.

As yet another alternative, U.S. Pat. No. 4,282,167 discloses the preparation of isocyanates using a modified Hofmann rearrangement reaction by reacting an alkali metal hypobromite or alkali metal hypochlorite with a solution of a substantially water-insoluble aliphatic or cycloaliphatic organic amide in a substantially water-immiscible organic solvent using a quaternary salt as a phase transfer catalyst. Unfortunately, the solubility of such alkali metal hypobromite and alkali metal hypochlorite salts is typically only about 5% by weight in water, and the purity levels of these salts is sometimes less than might be desired.

New, more efficient, non-phosgene processes for producing isocyanates would be highly desired by the isocyanates manufacturing community.

SUMMARY OF THE INVENTION

In one aspect, the present invention relates to a process for the preparation of an isocyanate compound, comprising:

(a) reacting an amide with an aqueous solution of hypochlorous acid in the presence of an water-immiscible organic solvent to produce an N-chloro amide; and (b) reacting said N-chloro amide with a base in the presence of a phase transfer catalyst and a water immiscible organic solvent to produce an isocyanate.

In another aspect, the present invention relates to the above process wherein steps (a) and (b) are carried out simultaneously in a single pot reactor.

In yet another aspect, the present invention relates to a process for producing an N-chloro amide by carrying out the reaction of step (a) above.

These and other aspects will become apparent upon reading the following detailed description of the invention.

DETAILED DESCRIPTION OF THE PREFERRED EMBODIMENTS

It has now been surprisingly found accordance with the present invention that hypochlorous acid is suitably employed in a simple reaction sequence to provide an isocyanate. The use of hypochlorous acid is advantageous since this acid is commercially available in excellent purity in high aqueous concentrations of 35% by weight or higher, considerably more concentrated than is available for the alkali metal hypochlorites (which is typically available at up to 5%) utilized in the prior art.

The amide used in the process of the present invention is suitably selected from any of the primary, secondary and tertiary amides, including mono-amides, diamides, substituted diamides, or other polyamides such as triamides, tetramides, and combinations thereof. Preferably, the organic amides employed are aliphatic, and the secondary aliphatic amides are preferred. By "secondary" aliphatic amide, it is meant that the alpha carbon atom is attached to two alkyl groups. Similarly, by "primary" it is meant that the alpha carbon atom is attached to only a single alkyl group. An example of a primary amide is n-heptanoyl amide, whereas cyclohexyl amide is an example of a secondary amide. Illustrative amides useful in the present invention include acetamide, butyl amide, iso-butyl amide, tertiary butyl amide, 2-norbornaneacetamide, n-octanoyl amide, n-heptanoyl amide, cyclohexanepropionamide, cyclohexyl amide, cycloheptylamide, 2-norbornylcarboxamide, 2-ethylhexanoylamide, sebacamide, 1,4-cyclohexyl dicarboxamide, and combinations thereof. The amide is preferably employed in a molar concentration of between about 0.05 molar and about 5 molar in the organic phase of the reaction mixture.

The base employed in the present invention is suitably an alkali metal hydroxide or oxide, such as NaOH, KOH or CaO. An aqueous solution of base or anhydrous base may be employed as desired. If an aqueous solution of the base is employed, a preferred concentration is between about 10 wt. % and about 60%, more preferably between about 20% and about 40%, based upon the total amount of water plus base in the aqueous solution of the base.

The phase transfer catalyst may be any organic quarternary ammonium or phosphonium salt, and these salts are well-known to function to promote phase transfer between an aqueous phase and an organic phase. Examples are: tetrabutyl ammonium bisulphate, tributyl phosphonium bromide, benzyl triethyl ammonium chloride and the like. Crown ethers and cryptates may also be used.

Illustrative phase transfer catalysts include the following: trioctyl methyl ammonium bromide, benzyl triethyl ammonium bromide, hexadecyltrimethyl ammonium bromide, trioctyl ethyl ammonium bromide, hexyl triethyl ammonium promide, hexadienyl triethyl ammonium bromide, dodecyl triethyl ammonium bromide, tridodecyl methyl ammonium chloride, didodecyl dimethyl ammonium chloride, trimethyl dodecyl ammonium chloride, tridodecyl pentyl ammonium bromide, trihexyl hecadecyl ammonium bromide, triododecyl benzyl ammonium chloride, trimethyl benzyl ammonium chloride, tetrabutyl phosphonium chloride, trioctyl ethyl phosphonium bromide, triethyl hexadecyl phosphonium bromide, hexadeoyl tributyl phosphonium bromide, tributyl decyl phosphonium bromide, tetraphenyl phosphonium bromide, and chloride and tetraphenyl arsonium chloride, and combinations thereof.

Suitable water-immiscible organic solvents include aliphatic, alicyclic, and aromatic hydrocarbons and chlorinated hydrocarbons such as methylene chloride, heptane, cyclohexane, toluene, benzene, and chlorobenzene, and combinations thereof. Esters or ethers can also be employed as solvents if desired.

The term water-immiscible, with respect to organic solvents mentioned above means that the solvent solubility in water is less than 50% (and preferably less than 10%) by weight at ambient room temperatures. The amide is considered to be water insoluble if its solubility is less than 50% (and preferably less than 10%) by weight at ambient room temperatures. At room temperatures the solubility of the phase transfer catalyst in the aqueous reaction phase should be at least 0.0001 molar and solubility in the organic phase should be at least 0.0001 molar. Preferably, catalyst solubility in the organic phase exceeds solubility in the aqueous phase.

The process of the present invention is suitably effected using reaction temperatures in the range of about 0° C. to 60° C., and preferably each step is effected at a temperature of between 0° C. and 10° C. with cooling. Although the reaction time can vary over a wide range, the preferred reaction time is less than an hour, more preferably between about 10 and about 30 minutes.

Unless otherwise specified herein, all percentage compositions are weight percent and all temperatures are degrees centigrade.

The following examples are intended to illustrate, but in no way limit the scope of, the present invention.

EXAMPLE 1

Preparation of T-Butyl Isocyanate

A slurry of 5.0 g (0.05 mol) of trimethyl acetamide in 50 ml of methylene chloride was stirred and cooled to 5° C. by means of an ice bath. To this mixture was added over a 5 minute period 9.4 g (0.055 mol) of a 30.6% aqueous solution of hypochlorous acid. At the end of the addition the temperature was 10° C. A 0.5 g quantity of tetrabutyl ammonium hydrogen sulfate was added to the mixture and it was cooled to 5° C. A solution of 2.2 g (0.055 mol) of sodium hydroxide in 10 ml water was then added to the stirred mixture over at 7 minute period. At the end of this addition, the temperature of the reaction mixture was 18° C. After stirring an additional 3 minutes, the methylene chloride layer was separated and analyzed by gas chromatography. This layer was found to contain t-butyl isocyanate in the amount equal to 83% of the theoretical yield.

EXAMPLE 2

Preparation of 3-Isocyanato Heptane

A. Preparation of 2- ethylhexyl carboxamide

With rapid stirring, 2-ethylhexanoyl chloride (50 g, 307 mmol) was added dropwise over 20 minutes to excess ammonium hydroxide (250 ml) that had been cooled to 0° in an ice bath. The bath was then removed and stirring continued for 90 minutes. The white solid product was recovered by filtration, washed three times with 50 ml portions of water and dried at 50° in a vacuum oven to give 36 g (82%) of the desired amide (m.p. 105°, lit. m.p. 101°–102°).

B. Preparation of N-chloro-2-ethylhexyl carboxamide 2-ethylhexyl carboxamide (35.75 g, 250 mmol) was suspended in 300 ml of ethyl acetate and cooled to 1°. Hypochlorous acid (43.3 g of 30.6% solution, 252 m mol) was added dropwise over 13 minutes with stirring. After 10 minutes, the cooling bath was removed and stirring continued for 1 hour while the mixture warmed to room temperature. The ethyl acetate layer was then separated and dried (MgSO$_4$) and the solvent was removed on the rotary evaporator and, finally, on the vacuum pump to give 44 g (98%) of colorless liquid N-chloro-2-ethylhexyl carboxamide.

C. Preparation of 3-isocyanatoheptane

N-chloro-2-ethylhexyl carboxamide (44 g, 250 m mol), methylene chloride (200 ml) and 5 mole percent (based on the amide) of tetrabutyl ammonium bisulphate phase transfer catalyst were stirred and cooled to 1° in an ice bath. A solution of sodium hydroxide (9.88 g, 250 mmol) in water (40 ml) was cooled below room temperature and added dropwise over about 8 minutes. Stirring was continued in an ice bath for 25 minutes, the organic and aqueous phases were than separated and the methylene chloride phase collected and dried (MgSO$_4$). After filtration, methylene chloride was removed on the rotary evaporator to give 33 g of colorless crude 3-isocyanatoheptane that assayed 92% by gas chromatography.

EXAMPLE 3

Preparation of 2-isocyanato pentane

A. Preparation of 2-methyl valeramide

Ammonium hydroxide (200 ml) was stirred and cooled in an ice bath to 0° and 2-methyl valeroyl chloride (48.46 g, 360 mmol) was added dropwise over 20 minutes. The resulting tan suspension was stirred for 40 minutes, filtered and the light tan solid product washed twice with 50 ml portions of cold water. After air drying overnight, 22 g of crude 2-methyl valeramide was obtained. An additional 12 g was recovered by evaporation of the filtrate.

B. Preparation of N-chlor-2-methyl valeramide

A stirred suspension of 2-ethyl valeramide (33.0 g, 286 mmol) in 220 ml of ethyl acetate was cooled to 0° and hypochlorous acid (55.25 g of 27.67% solution, 291 mmol) was added over 15 minutes. The cooling bath was removed and stirring continued for ½ hour. The organic phase was collected and dried (MgSO$_4$) and the solvent was removed on a rotary evaporator to yield 32.8 g of N-chloro-2-methyl valeramide as a clear yellow liquid.

Preparation of 2-isocyanatopentane

N-chloro-2-methyl valeramide (32.45 g, 216 mmol), methylene chloride (200 ml) and tetrabutyl ammonium bisulphate as phase transfer catalyst (1.5 g, 2 mole percent based on the amide) were stirred and cooled to 0° C. Sodium hydroxide (8.69 g, 217 mmol) dissolved in cold water (25 ml) was added dropwise over about 8 minutes. The mixture was stirred in the cold for 35 minutes, the organic layer was collected and dried (MgSO$_4$) and the solvent removed on a rotary evaporator to yield 20.6 g of crude 2-isocyanatopentane that showed an assay of 83% by gas chromatography.

EXAMPLE 4

Preparation of 2-Methyl-2-Isocyanato Pentane

A. Preparation of 2,2-dimethyl valeroyl chloride 2,2-dimethyl valeric acid (49.0 g, 377 mmol) was added dropwise over 1 hour with stirring to freshly distilled thionyl chloride (102 g, 860 mmol) that was cooled in a water bath. After stirring for an additional ½ hour in a warm water bath, excess thionyl chloride was removed by distillation and the crude acid was then fractionally distilled to give 49.7 g of product that assayed >95% by gas chromatography, bp 45°/10.5 mm (lit. bp 45°/10 mm).

B. Preparation of 2,2-dimethyl valeramide

Ammonium hydroxide (250 ml) was stirred and cooled to 1° C. and 2,2-dimethyl valeroyl chloride (49.7 g, 95%, 318 mmol) was added dropwise over 30 minutes. After stirring at room temperature for an additional ½ hour, the white solid product was recovered by filtration, washed with water and allowed to air dry to give 35.4 g (86%) of the desired amide, mp 94°-95° (lit. mp 95°-96° C.).

C. Preparation of N-chlor-2,2-dimethyl valeramide

A stirred suspension of 2,2-dimethyl valeramide (35 g, 271 mmol) in ethyl acetate (200 ml) was cooled to 0° C. and hypochlorous acid (40.0 g of 36.2% solution, 276 mmol) was added dropwise over 12 minutes. The resulting clear yellow solution was then stirred for 30 minutes at room temperature, the organic phase separated and dried (MgSO$_4$) and the ethyl acetate removed in vacuo to give 39.35 g of low-melting solid product.

D. Preparation of 2-methyl-2-isocyanatopentane

N-chloro-2,2-dimethyl valeramide (20.0 g, 122 mmol), methylene chloride (200 ml) and tetrabutyl ammonium bisulphate (1.0 g, 2.4 mole percent based on the amide) were stirred and cooled to 0° C. A solution of sodium hydroxide (4.89 g, 122 mmol) in cold water (15 ml) was then added over 10 minutes. The mixture was stirred in an ice bath for one-half hour, the organic phase was separated and dried (MgSO$_4$) and the solvent removed on a rotary evaporator to give 14.7 g of liquid product that assayed 75% by GC.

EXAMPLE 5

Preparation of 2-isocyanato decane

A. Preparation of 2-methyl decanoic acid

Sodium (12.5 g, 0.54 g-atoms) was gradually added in small pieces to absolute ethanol (375 ml) while stirring under an inert (N2) atmosphere until complete solution of the sodium has taken place. Diethyl methylmalonate (95.5 g, 570 mmol) was then added dropwise to the sodium ethoxide solution over 20 minutes and the mixture was heated at reflux for about 15 minutes. After cooling to room temperature, 1-bromooctane (99 g, 512 mmol) was added dropwise over 15 minutes; the mixture was heated at reflux for 2 hours, cooled and neutralized by adding a few drops of glacial acetic acid. About two-thirds of the alcohol was removed by distillation and the residue was washed with 500 ml of water. The organic phase was separated and the aqueous phase extracted with three 50 ml portions of benzene. The organic phase and extracts were combined, washed with water, and dried over anhydrous magnesium sulfate. The residue obtained upon evaporation of the solvent was treated with a solution of 115 g of 86% potassium hydroxide Pellets in 900 ml of reagent ethanol and the mixture heated at reflux, with stirring, for 4 hours. About two-thirds of the solvent was removed by distillation, 750 ml water was added, followed by sufficient (520 ml) 6N sulfuric acid to bring the pH of the solution to 1-2. The organic phase was separated and the aqueous phase was extracted with two portions of ether. The organic phase and extracts were combined, washed with water, then with saturated sodium chloride solution, and finally dried over magnesium sulfate. The residue obtained upon evaporation of the solvent was heated to 180°-190° C. at which temperature decarboxylation occurred smoothly over a period of several minutes. The crude acid was then distilled through a short Vigreux column to give 64 g of product (73% yield), b.p. 143°/5.8 mm (lit. b.p. 137°/4.4 mm), which showed a purity of >99% by GC.

B. Preparation of 2-methyl decanoyl chloride

To thionyl chloride (93 g, 782 mmol), cooled to 15° C. in a water bath was added during 1 hour 2-methyl decanoic acid (64 g, 344 mmol). The cold water bath was removed and the mixture was heated at 50° C. with stirring for 45 minutes. The excess thionyl chloride was removed by distillation and the crude acid chloride was then fractionally distilled (b.p. 143°-45° C./5.8 mm) to give 69 g of product (99% yield) that showed an assay of >98% by GC.

C. Preparation of 2-methyl decanamide

2-Methyl decanoyl chloride (68.9 g, 336 mmol) was added dropwise to rapidly stirred ammonium hydroxide (200 ml) cooled in an ice bath. The resulting white slurry was stirred at room temperature for one-half hour, then filtered through a Buchner funnel. The filter cake was washed with 100 ml of ice water, air-dried overnight, then dried in a vacuum over at 55° C. for 2 hours to give 53 g (85.5% yield) of a white solid product, m.p. 80°-81° C. (lit. m.p. 81.4° C.).

D. Preparation of N-chloro-2-methyl decanamide

2-Methyl decanamide (50 g, 270 mmol) was suspended in 300 ml of methylene chloride, cooled to 2° C. and aqueous HOCl (14.72 g, 280 mmol) was added over about 10 minutes. The mixture was stirred in the cold for 15 minutes, then at room temperature for 45 minutes. The methylene chloride layer was separated, dried over magnesium sulfate, and the solvent removed on a rotary evaporator in a warm water bath to give 56 g (94% yield) of white solid product, m.p. 56°-57° C.

E. Preparation of 2-isocyanatodecane

N-chloro-2-methyl decanamide (26.0 Og, 118 mmol) was dissolved in 250 ml of methylene chloride and cooled to 2° C. in an ice bath. Tetrabutyl ammonium hydroxide (1 g, 2.5 mole percent based on amide) was added, followed by sodium hydroxide (4.74 g, 119 mmol) dissolved in 40 ml of ice water. The mixture was stirred in the cold for 25 minutes and the organic layer was collected and dried over magnesium sulfate. Removal of solvent gave 21.6 g of liquid product.

The above reaction was repeated using the same amounts of reactants and the same conditions; the products were combined to give 44 g of crude material that showed an assay of >90% by GC. This was fractionally distilled (b.p. 92° C./4.0 mm) to give 28.2 g (65% yield) of 2-methyl isocyanatodecane that showed a purity of >99% by GC; the structure was confirmed by nmr analysis. (Calculated for C11H21NO:C, 72.1%; H, 11.5%; N, 7.6%. Found: C, 67.4%; H, 11.4%; N, 8.4%).

EXAMPLE 6

Preparation of 2,9-dimethyl-2,9-diisocyanatodecane

A. Preparation of 2,2,9,9-tetramethyl-1,10-diphenyldecane-1,10-dione

This precursor, $C_6H_5C(O)C(CH_3)_2-(CH_2)_6-C(CH_3)_2C(O)C_6H_5$ was prepared by reacting isobutyrophenone with sodium amide followed by treatment with 1,6-dibromohexane.

B. Preparation of 2,2,9,9-tetramethyl sebacic acid diamide

The dione from step 1 (82.2 g, 217 mmol) was added to 4 equivalents of sodium amide suspended in toluene (600 ml). After heating at reflux for 1 hour, the mixture was cooled and 500 ml of water was added. The white solid product was recovered by filtration, washed with water and dried to give 35 g (65%) of the diamide which, when crystallized from ethanol, showed a melting point of 211°-214° C. (lit.m.p 210°-213° C.).

C. Preparation of N,N'-dichloro-2,2,9,9-tetramethyl sebacic acid diamide

The diamide from step 2 (12.8 g, 50 mmol) was suspended in methylene chloride (200 ml) and treated in the cold with 2 equivalents of HOCl (5.25 g, 100 mmol) as a 27.8% aqueous solution. After stirring for several hours at room temperature, the white crystalline product was received by filtration and dried in vacuo to give 10.0 g (62%) of the N,N'-dichlorodiamide, m.p. 115°-116° C. (Calculated for C14H26Cl2N2O2:C,51.6%; H, 8.0%; N,8.6%. Found: C, 50.0%; H, 7.7%; N, 8.0%).

D. Preparation of 2,9-dimethyl-2,9-diisocyanatodecane

Two runs were conducted, each on a 5-g scale, as follows: the N,N'-dichlorodiamide from step 3 (5.0 g, 15.4 mmol) was suspended in 150 ml of methylene chloride and cooled with stirring to 1° C. Tetrabutyl ammonium bisulphate (0.3 g, 5 mole % based on amide) was then added followed by sodium hydroxide (1.25 g, 31.2 mmol) dissolved in 5 ml of ice water. After stirring in cold water for 30 minutes, the organic phase was separated and dried and the methylene chloride solvent was removed on the rotary evaporator to give 3.45 g, (88%) of colorless liquid product that showed a diisocyanate content of 91% by GC assay. This material and the like product from the second reaction were combined and fractionally distilled (bp 109°-110° C. at 0.5 mm) to give 4.92 g (65% yield) of product that showed an assay of >99% (calculated for C14H24N2O2: C, 66.6$; H, 9.6%; N, 11.15%. Found: C, 65.35%, H, 9.4%; N, 11.4%).

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process for preparation of an isocyanate comprising:
   (a) reacting an amide with an aqueous solution of hypochlorous acid in the presence of an water-immiscible organic solvent to produce an N-chloro amide; and
   (b) reacting said N-chloro amide with a base in the presence of a phase transfer catalyst and a water immiscible organic solvent to produce an isocyanate, wherein step (a) and step (b) are each carried out at a reaction temperature of between about 0° C. and about 50° C.

2. The process of claim 1 wherein the hypochlorous acid is present in the aqueous solution in a concentration of from about 5 to about 50% by weight based upon the total weight of water plus hypochlorous acid in said aqueous solution.

3. The process of claim 1 wherein the hypochlorous acid is present in the aqueous solution in a concentration of from about 25 to about 35% by weight based upon the total weight of water plus hypochlorous acid in said aqueous solution.

4. The process of claim 1 wherein the organic solvent is selected from the group consisting of methylene chloride, ethyl acetate, cyclohexane, benzene, and combinations thereof.

5. The process of claim 1 wherein step (a) and step (b) are each carried out at a reaction temperature of between about 0° C. and about 10° C.

6. The process of claim 1 wherein the reactions of step (a) and step (b) are each carried out using a reaction time of between about 10 minutes and about 60 minutes.

7. The process of claim 1 wherein the base is an alkali metal hydroxide or oxide.

8. The process of claim 1 wherein steps (a) and (b) are carried out simultaneously in a single pot reactor.

* * * * *